United States Patent

Sawano et al.

[11] 4,310,685
[45] Jan. 12, 1982

[54] PROCESS FOR PREPARING BRASSYLIC DIESTER

[75] Inventors: Kiyohito Sawano, Hiratsuka; Toyohiko Kobayashi; Haruki Tsuruta, both of Yokohama, all of Japan

[73] Assignee: Takasago Perfumery Co., Ltd., Tokyo, Japan

[21] Appl. No.: 123,246

[22] Filed: Feb. 21, 1980

[30] Foreign Application Priority Data

Feb. 26, 1979 [JP] Japan .................................. 54-21575

[51] Int. Cl.$^3$ ............................................. C07C 67/42
[52] U.S. Cl. .................................... 560/204; 560/190
[58] Field of Search ................. 260/412.9 R, 410.9 E, 260/410.9 L, 410.9 Q, 343; 560/204, 190

[56] References Cited

U.S. PATENT DOCUMENTS 3,072,680  1/1963  Starcher ...................... 260/410.9 R
3,849,457 11/1974  Haag ................................... 260/413

OTHER PUBLICATIONS

*Organic Reactions* vol. 9, pp. 73–106, John Wiley & Sons Inc. (1957).

Primary Examiner—John F. Niebling
Attorney, Agent, or Firm—Sughrue, Mion, Zinn, Macpeak and Seas

[57] ABSTRACT

A process for preparing a brassylic diester of the formula:

$$ROOC-(CH_2)_{11}COOR$$

wherein R is a lower alkyl group by hydrocracking 6,6'-methylenebis-(6-hexanolide) in an alcohol of the formula:

$$ROH$$

(wherein R is as defined above) in the presence of a metal catalyst and an acid catalyst. A process for producing the hexanolide is also disclosed.

7 Claims, No Drawings

PROCESS FOR PREPARING BRASSYLIC DIESTER

BACKGROUND OF THE INVENTION

1. Field of the Invention

This invention relates to a novel process for preparing a brassylic diester of the formula (I):

$$ROOC-(CH_2)_{11}-COOR \quad (I)$$

wherein R is a lower alkyl group.

2. Description of the Prior Art

A brassylic diester can be hydrolyzed to brassylic acid and the two compounds are not only useful as a material for producing macrocyclic esters important as perfume musks but also they find much utility as materials for producing various polymers (e.g., polyamides, polyesters, etc.) and as plasticizers for polyvinyl chloride, polychloroethylene, etc.

Brassylic acid and esters are conventionally produced by oxidizing erucic acid in rapeseed oil with ozone or permanganic acid. However, it is becoming increasingly difficult to produce them from naturally occurring materials because the price of the rapeseed depends on the yield of its harvest, the acreage of rape fields in the world is decreasing, and Canada the world's largest rape producer is growing an increasing volume of a species with a small content of erucic acid.

Known processes for the synthesis of brassylic acid are (1) heating methyl undecylenate and ditertiary butyl peroxide in acetic acid for 48 hours, followed by hydrolyzing the reaction product (U.S. Pat. No. 3,308,140); (2) heating 2-ethoxycarbonylcyclododecanone with caustic alkali in diethylene glycol, followed by rendering the product acidic (Japanese Patent Publication No. 34406/71); and (3) reacting ethyl cyanoacetate with Br-(CH$_2$)$_{10}$COOC$_2$H$_5$ in dimethylformamide, hydrolyzing the reaction product, followed by decarboxylation of the hydrolyzate [Dudinov A. A. et al., *Izv. Akad. Nauk SSSR, Ser. Khim.*, 1974 (6), 1421-1423 (*Chem. Abstracts*, 81, 91013t, 1974)]. However, these processes are not necessarily acceptable as an industrial process primarily because the starting materials are not readily available.

Accordingly, various studies have been conducted directed to an industrial process for producing brassylic acid and it has now been found that brassylic diester can be easily prepared from 6,6'-methylenebis-(6-hexanolide) that is readily obtainable from available petrochemical products, and a method for preparing a high yield of 6,6'-methylenebis-(6-hexanolide) from 2,2'-methylenebiscyclohexanone has also been discovered.

DETAILED DESCRIPTION OF THE INVENTION

The process of this invention follows the reaction scheme represented below:

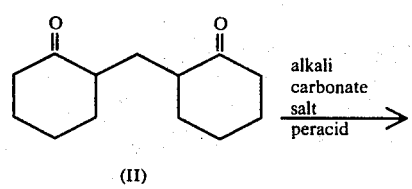

(II)

-continued

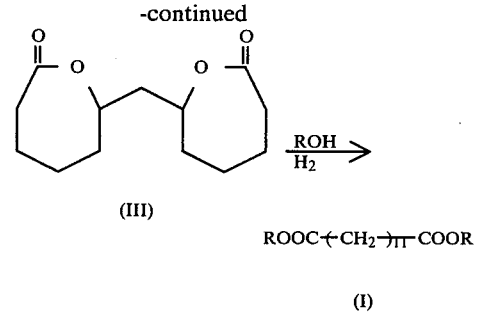

(III)

$$ROOC-(CH_2)_{11}-COOR$$

(I)

wherein R is a lower alkyl group, e.g., a (C$_1$-C$_4$)alkyl group.

Stated more specifically, the process of this invention comprises reacting a peracid with 2,2'-methylenebiscyclohexanone (II) in a halogenated organic solvent in the presence of an alkali carbonate salt to form 6,6'-methylenebis-(6-hexanolide) (III) which is then treated with pressurized hydrogen in alcohol in the presence of a metal catalyst and an acid catalyst to thereby form a brassylic diester (I).

The starting material for this process, 2,2'-methylenebiscyclohexanone (II), can readily be prepared by reacting paraldehyde with cyclohexanone that is cheaply available as a petrochemical product [see J. Mounet et al., *Bull. Soc. Chim. Fr.*, pp. 1170-1173 (1970)].

A method is known of producing 6,6'-methylenebis-(6-hexanolide) (III) from 2,2'-methylenebiscyclohexanone (II) by reacting a solution of permaleic acid in methylene chloride with a solution of the compound (II) in methylene chloride which is added dropwise at a temperature between 15° and 25° C. [J. Kondelivova et al., *Collection of Czechoslovak Chemical Communication*, 37, 263-269 (1972)]. The method involves the "Baeyer-Villiger reaction" which is an oxidation with a peracid and is described in detail in Roger Adams, *Organic Reactions*, Vol. 9, pp. 73-106, John Wiley & Sons Inc., 1957. However, the yield of the product obtained by this method is only 43%, and as a consequence, the steps for converting the compound (II) to (III) have presented a bottleneck to the conventional commercial production of a brassylic diester (I) from the biscyclohexanone.

As a result of studies directed to a synthesis which eliminates this defect, it has been found that the yield of the compound (III) is substantially doubled by reacting the compound (II) with a peracid in a halogenated organic solvent in the presence of an alkali carbonate salt.

According to this invention, the oxidation of compound (II) is carried out under conditions generally the same as the conditions for the Baeyer-Villiger reaction except for the use of an alkali carbonate salt. Illustrative halogenated organic solvents include methylene chloride, chloroform, dichloroethane and carbon tetrachloride. Suitable amounts for the solvent are about 5 to 50 times the volume of the reactant. Examples of the peracid are peracetic acid, perbenzoic acid, permaleic acid, and monoperphthalic acid. The peracid is preferably used in an amount two to three times the molar amount of the compound (II). Preferred examples of the alkali carbonate salt are the powders of anhydrous sodium carbonate and potassium carbonate. The alkali carbonate salt is preferably used in an amount four to six tims the molar amount of the compound (II).

In operation, a compound of formula (II) and an alkali carbonate salt are dissolved in a halogenated organic solvent (concentration of compound (II): 5 to 100% and preferably 10 to 30% by volume; amount of carbonate: about 1 to 5 and preferably 2 to 3 times the weight of compound (II)). The solution is cooled to a temperature between about 20° and 25° C., a solution of a peracid (2 to 2.6 and more preferably 2.2 to 2.4 molar equivalents) in a halogenated organic solvent (0.5 to 10 and preferably 1 to 2 times the acid by volume) is added to the solution in small aliquots over a period of 2 to 3 hours, and the reaction mixture is stirred for a few hours with the temperature held between 20° and 25° C. The reaction mixture is then washed with water and extracted with ether. The extract is washed with 2 to 3% aqueous sodium carbonate or saturated aqueous sodium chloride, dried, and the solvent is distilled off. The resulting crude crystal is recrystallized from isopropyl ether to give 6,6'-methylenebis-(6-hexanolide) of the formula (III) in a yield of about 80%.

Compound (III) is then converted to a brassylic diester. U.S. Pat. No. 3,849,457 describes a method for producing a carboxylic acid by hydrocracking a lactone compound. This method can be used to hydrocrack the compound of the formula (III) to form brassylic acid. However, in addition to the difficulty in controlling the reaction due to solidification of brassylic acid product that melts at temperatures as high as 113.5° C., the presence of by-products such as the oxy acid and unsaturated acids in the reaction product requires repeated recrystallizations for isolating and purifying brassylic acid.

As a result of studies on a method to overcome this defect of the conventional technique, it has been unexpectedly found that by hydrocracking the compound (III) in alcohol, a high yield of brassylic diester (I) can be obtained by a very simple operation. The reaction is performed in the presence of both a metal catalyst and an acid catalyst. According to U.S. Pat. No. 3,849,457, when an ester compound or lactone compound is hydrocracked, a carboxylic acid compound is formed. The teachings of the patent lead one to conclude that the hydrocracking of compound (III) in an alcohol produces brassylic acid which is first esterified in the presence of an acid catalyst to a brassylic diester and the brassylic diester is most likely decomposed to brassylic acid. Therefore, it is entirely unexpected that the reaction according to the present invention gives rise to the brassylic diester in a high yield without its subsequent decomposition to brassylic acid. What is more, the thus prepared brassylic diester can be purified by fractional distillation and other suitable means to provide a product of high purity which may be hydrolyzed to form brassylic acid of high purity. Therefore, the process of this invention involving such a reaction is very advantageous in the production of brassylic acid.

The metal catalysts used in the process of this invention may be the same as those specified in U.S. Pat. No. 3,849,457 and illustrative catalysts are metals of group Ib (copper group) of the Periodic Table, group IIb (zinc group), group IIIb (aluminum group), group IVa (titanium group), group Va (vanadium group), group VIa (chromium group), group VIIa (manganese group), and group VIII (iron and platinum groups). For higher yield and product's purity, metals of the group VIII are preferred and, especially, commercial reducing catalysts such as Raney nickel or palladium- or platinum-on-activated carbon are used to advantage. A suitable amount of the metal catalyst is about 0.1 to 30%, preferably 5 to 10% by weight based on the compound (III).

The acid catalysts used in the process of this invention may also be the same as those specified in U.S. Pat. No. 3,849,457, such as alumina, silica-alumina, silica-magnesia, silica-alumina-magnesia, vanadia, zirconia, chromia, chromia-alumina, crystalline alumina-silicate sucy as HY type zeolite, a strongly acidic cation exchange resin, polyphosphoric acid, and paratoluenesulfonic acid. A strongly acidic cation exchange resin such as Amberlist 15 (manufactured by Rohm & Haas) and paratoluenesulfonic acid are particularly preferred. A suitable amount of the acid catalyst is about 0.1 to 30%, preferably 5 to 10% by weight based on the compound (III).

Illustrative alcohols used as solvent are aliphatic lower ($C_1$-$C_4$) alcohols such as methanol, ethanol, n-propanol, isopropanol and tert-butanol. Such alcohols may be used in an amount 10 to 20 times the volume of the compound (III) with advantage.

The process of this invention is started at a hydrogen pressure in the range of from about 5 to 50 kg/cm$^2$, preferably about 20 to 30 kg/cm$^2$, and as the temperature increases the pressure preferably increases to a level between 50 and 150 kg/cm$^2$. The reaction temperature is between about 25° and 350° C., preferably about 150° to 250° C., and the reaction time is between 3 and 25 hours, preferably between 4 and 15 hours.

The reaction mixture is freed of the catalysts by filtration, extracted with ether, and the extract is washed with dilute aqueous sodium carbonate and saturated aqueous sodium chloride, dried, and distilled to provide a brassylic diester of the formula (I).

This invention is now described in greater detail by reference to the following reference example and examples, which are given here for illustrative purposes only and are by no means intended to limit the scope of the invention.

REFERENCE EXAMPLE

Preparation of 2,2'-methylenebiscyclohexanone

A mixture comprising 68 g of paraldehyde, 6 g of caustic potash and 188 g of methanol was added dropwise to a solution comprising 1,000 g of cyclohexanone and 188 g of methanol at 60°–70° C. over a period of 2 hours, and the resulting mixture was stirred for another 3 hours at 60°–70° C. Thereafter, the reaction mixture was decomposed with dilute hydrochloric acid, extracted with ether, washed first with 3% aqueous sodium carbonate, then with saturated aqueous sodium chloride, and dried over anhydrous magnesium sulfate. After recovering the solvent, the dried product was distilled under vacuum to provide 340 g (yield: 64%) of a fraction boiling at 135°–145° C./3 mm Hg.

EXAMPLE 1

Production of 6,6'-methylenebis-(6-hexanolide)

To a mixture comprising 20.8 g of 2,2'-methylenebiscyclohexanone and 50 g of powdered anhydrous sodium carbonate, 100 ml of ethylene dichloride was added with stirring. To the resulting solution, a mixture comprising 47.5 g of 40% peracetic acid and 50 ml of ethylene dichloride was added dropwise at 20°–25° C. over a period of about 2 hours. Following stirring for another 3 hours, the reaction mixture was washed first with water, then with a saturated Mohr's salt solution to decompose unreacted peracetic acid, and extracted with ether. The extract was washed with 2% aqueous sodium carbonate once, then washed with saturated aqueous sodium chloride, and the organic phase was dried over anhydrous magnesium sulfate. Concentration of the dried product gave 20.5 g of crude 6,6'-methylenebis-(6-hexanolide). Recrystallizing the crude product from isopropyl ether gave 19.0 g (yield: 79%) of a white crystal of 6,6'-methylenebis-(6-hexanolide) melting at 108°–109° C.

EXAMPLE 2

An autoclave charged with 5 g of 6,6'-methylenebis-(6-hexanolide), 0.5 g of 2% palladium on granular carbon, 0.5 g of Amberlist 15 and 100 ml of methanol was heated at 200° C. for a period of 15 hours with an initial hydrogen pressure of 30 kg/cm$^2$. When the reaction was carried out at 200° C., a maximum gauge pressure of 110 kg/cm$^2$ was obtained. The reaction mixture was freed of the solvent by filtration and extracted with ether. The extract was washed first with 2% aqueous sodium carbonate, then with saturated aqueous sodium chloride. Following drying over anhydrous magnesium sulfate, the product was distilled to give 4.7 g (yield: 82.6%) of an oily product boiling at 140°–145° C./1 mm Hg and having the following physical properties that agree with those of a commercial grade of dimethyl brassylate.

m.p.: 33° C.

IR (KBr): 2920, 2850, 1736, 1438, 1170 cm$^{-1}$

NMR (C$_6$D$_6$): δ 1.30 (6s, 18H), 1.9–2.4 (m, 4H), 3.58 (s, 6H) ppm

MS: m/e 272, 241, 208, 199, 167, 149, 126, 125, 112, 111, 98, 97, 87, 84, 83, 74

EXAMPLE 3

An autoclave charged with 5 g of 6,6'-methylenebis-(6-hexanolide), 0.5 g of Raney nickel, 0.5 g of Amberlist 15 and 50 ml of methanol was heated at 200° C. for a period of 15 hours with an initial hydrogen pressure of 30 kg/cm$^2$. When the reaction was carried out at 200° C., a maximum gauge pressure of 96 kg/cm$^2$ was recorded. By treating the reaction mixture in the same manner as in Example 2, 4.9 g (yield: 86.5%) of dimethyl brassylate was provided.

EXAMPLE 4

An autoclave charged with 5 g of 6,6'-methylenebis-(6-hexanolide), 0.5 g of 5% rhodium on carbon, 0.5 g of Amberlist 15 and 100 m of methanol was heated at 200° C. for a period of 15 hours with an initial hydrogen pressure of 30 kg/cm$^2$. When the reaction was carried out at 200° C., a maximum gauge pressure of 78 kg/cm$^2$ was obtained. By treating the reaction mixture in the same manner as in Example 2, 4.9 g (yield: 86.5%) of dimethyl brassylate was provided.

While the invention has been described in detail and with reference to specific embodiments thereof, it will be apparent to one skilled in the art that various changes and modifications can be made therein without departing from the spirit and scope thereof.

What is claimed is:

1. A process for preparing a brassylic diester of the formula:

$$ROOC-(CH_2)_{11}-COOR$$

wherein R is a lower alkyl group which comprises hydrocracking 6,6'-methylenebis-(6-hexanolide) in an alcohol of the formula:

$$ROH$$

wherein R is as defined above, in the presence of a metal catalyst and an acid catalyst.

2. The process according to claim 1, wherein the metal catalyst consists of a metal of the group VIII of the Periodic Table.

3. The process according to claim 1, wherein the acid catalyst consists of a strongly acidic cation exchange resin or paratoluenesulfonic acid.

4. A process for preparing a brassylic diester of the formula:

$$ROOC-(CH_2)_{11}-COOR$$

wherein R is a lower alkyl group which comprises reacting a peracid with 2,2'-methylenebiscyclohexanone in a halogenated organic solvent in the presence of an alkali carbonate salt to form 6,6'-methylenebis-(6-hexanolide), and hydrocracking said hexanolide in an alcohol of the formula:

$$ROH$$

wherein R is as defined above, in the presence of a metal catalyst and an acid catalyst.

5. The process according to claim 4, wherein the metal catalyst consists of a metal of the group VIII of the Periodic Table.

6. The process according to claim 4, wherein the acid catalyst consists of a strongly acidic cation exchange resin or paratoluenesulfonic acid.

7. The process according to claim 4, wherein the peracid is peracetic acid.

* * * * *